United States Patent [19]
Wiley et al.

[11] Patent Number: 5,104,620
[45] Date of Patent: Apr. 14, 1992

[54] DISPOSABLE ALLERGY SKIN TESTING KIT

[76] Inventors: Fred R. Wiley, 11735 Shadowglen Rd., El Cajon, Calif. 92020; Milan L. Brandon, 2800 Third Ave., San Diego, Calif. 92103

[21] Appl. No.: 559,660

[22] Filed: Jul. 30, 1990

[51] Int. Cl.⁵ .................................. A61B 5/00
[52] U.S. Cl. .................................. 422/61; 128/743; 424/9; 604/46; 604/47
[58] Field of Search .................. 422/61; 128/743; 604/46, 47, 173; 424/9

[56] References Cited

U.S. PATENT DOCUMENTS

| | | | |
|---|---|---|---|
| 2,817,336 | 12/1957 | Kravitz et al. | 604/47 |
| 2,841,138 | 7/1958 | Laub | 128/743 |
| 2,893,392 | 7/1959 | Wagner et al. | 128/743 X |
| 2,974,787 | 3/1961 | Cooper | 604/47 X |
| 4,473,083 | 9/1984 | Magnias | 128/743 |
| 4,711,247 | 12/1987 | Fishman | 128/743 |

FOREIGN PATENT DOCUMENTS

| | | | |
|---|---|---|---|
| 2909349 | 9/1980 | Fed. Rep. of Germany | 128/743 |
| 2940342 | 4/1981 | Fed. Rep. of Germany | 604/46 |
| 0009149 | 12/1988 | World Int. Prop. O. | 128/743 |

Primary Examiner—Robert J. Hill, Jr.
Attorney, Agent, or Firm—Charles C. Logan, II

[57] ABSTRACT

A disposable allergy skin testing kit that is formed from a top layer sheet, a membrane sheet, and a bottom layer sheet. The bottom sheet has a plurality of recesses formed at predetermined locations to form chambers into which a predetermined antigen has been deposited. The membrane sheet covers these chambers and forms a liquid tight seal. The top layer sheet has an aperture formed in it above each of the antigen chambers. A pushbutton needle assembly is mounted in each of these apertures and it has a disk-shaped pushbutton with a needle extending downwardly from its bottom surface. Flexible support arms attached to the edge of the apertures and the disk-shaped pushbutton allow it to be depressed a sufficient distance in order to rupture the antigen chamber and travel downwardly entirely through it so that the needle penetrates into the patient's skin taking antigen with it. A protector sheet is removably received between the top layer sheet and the membrane sheet prior to the allergy skin testing kit being used.

7 Claims, 1 Drawing Sheet

DISPOSABLE ALLERGY SKIN TESTING KIT

BACKGROUND OF THE INVENTION

The invention relates to allergy testing and more specifically to a disposable allergy skin testing kit.

Presently most allergy testing is done by the prick test method or the intra-dermal test method. The prick test involves putting a drop of antigen on the skin of a person, then pricking the skin just enough to break it and let the antigen be absorbed into the tissue to see if a reaction occurs. The intra-dermal test method requires the antigen to be injected under the skin into the dermal layer, which is a deeper layer of skin.

One of the most prevelant type of prick test equipment uses disposable allergy test needles whose tips have been dipped into a tray that holds up to 96 wells of antigen extract.

It is an object of the invention to provide a novel disposable allergy skin testing kit that eliminates the need for buying individual disposable allergy test needles.

It is another object of the invention to provide a novel disposable allergy skin testing kit that eliminates the need for using a tray that holds up to 96 wells of antigen extract.

It is also an object of the invention to provide a novel disposable allergy skin testing kit that can be sold in a card like form that can be placed upon the patient's skin and pushbutton needle assemblies on the card can be pressed downwardly to rupture an antigen chamber thereunder and also pass through the bottom of the card to prick the skin of the patient. These test kit cards can be manufactured with predetermined groups of antigens.

It is another object of the invention to provide a novel disposable allergy skin testing kit that is economical to manufacture and market.

SUMMARY OF THE INVENTION

The disposable allergy skin testing kit contains all of the material necessary for allergy skin testing, including the allergens. The card like kit has twelve or more skin tests that may be administered in one application, each skin test being approximately one inch apart. The antigen is in a small sealed chamber through which the needle penetrates and then into the skin taking antigen with it, somewhat analagous to a bee sting, to complete the skin test. The card like unit is of a constant size and shape to allow use of a standard transparent template pre-marked with the name of the antigen at each site and a central point sitting over the center of each test skin site to facilitate drawing the size of each skin test reaction on the template. Presently there is no comparable skin testing kit on the market.

The novel disposable allergy skin testing kit is formed from a bottom layer sheet, a membrane sheet, and a top layer sheet. The top surface of the bottom layer sheet has a plurality of recesses or pockets formed in it into which a specific antigen is placed. The membrane sheet is attached to the top surface of the bottom layer sheet to form a liquid tight seal. The top layer sheet has an aperture positioned immediately above each of the antigen chambers. A pushbutton needle assembly is mounted in each of these apertures and they are formed of a disk-shaped pushbutton having radially extending flexible support arms secured to the walls of the aperture. A needle extends downwardly from the bottom surface of the disk-shaped pushbutton. The flexible support arms allow the pushbutton to be depressed a sufficient distance to penetrate the membrane sheet and its antigen chamber and also pass completely therethrough in order to prick the skin of the patient.

At least two or more edges of the respective sheet members are heat sealed or otherwise fastened to each other to form an open space between the bottom surface of the top layer sheet and the top surface of the membrane sheet. A protective sheet may be removably inserted into this open space so that the needle cannot penetrate the membrane sheet before it is to be used.

The bottom layer sheet and the membrane sheet are preferably made of a metallic material such as aluminum foil but they can also be made of plastic. The top layer sheet would normally be made of plastic material.

One of the test kit cards could have all similar antigens such as grasses, weeds, molds, foods, etc. in their chambers. By positioning a template over the patients test site, an immediate reading can be taken as to which antigen the patient has had a reaction.

DESCRIPTION OF THE PREFERRED EMBODIMENT

Figure 1:
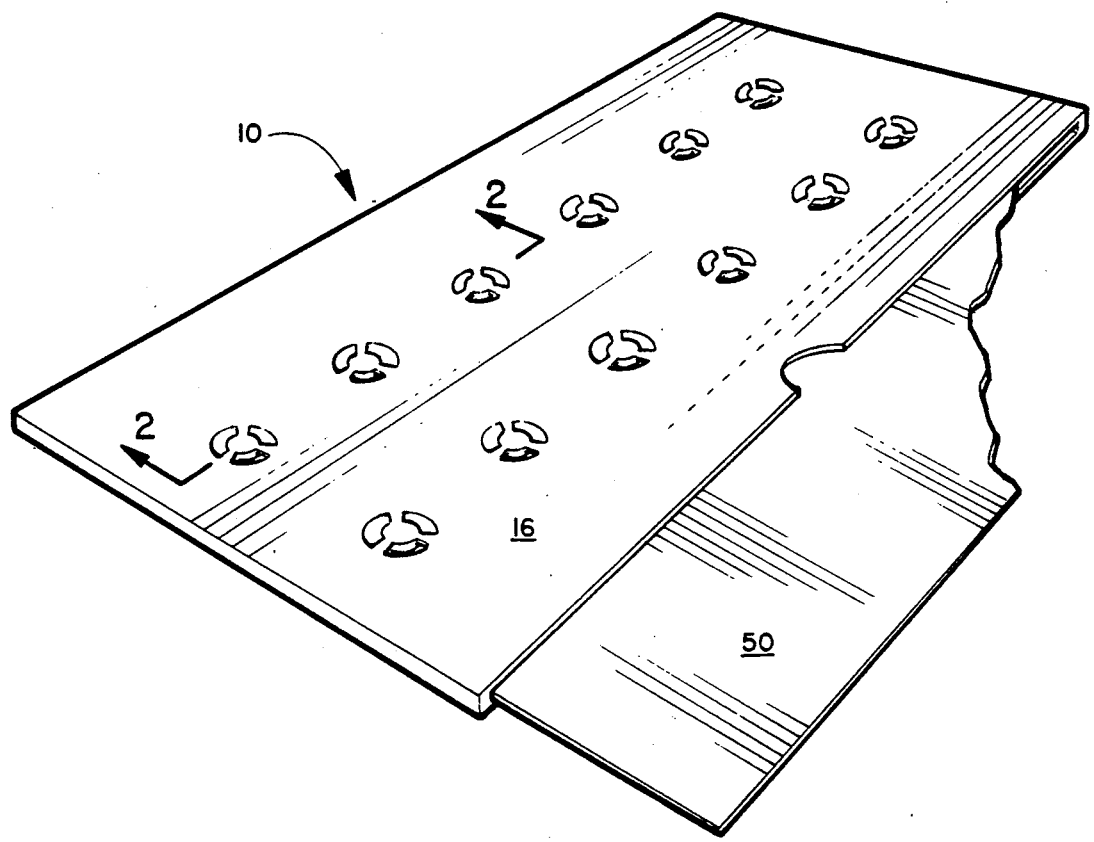
FIG. 1 is a front perspective view of applicant's novel allergy skin test kit.
Figure 2:
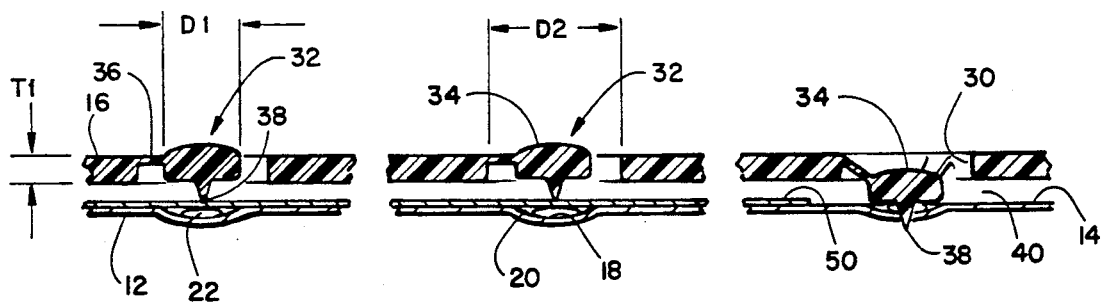
FIG. 2 is an enlarged cross sectional view taken along lines 2—2 of FIG. 1.

Applicant's novel disposable allergy skin testing kit will now be described by referring to FIGS. 1 and 2. The disposable allergy skin testing kit is generally designated numeral 10.

The skin testing kit 10 has a bottom layer sheet 12, a membrane sheet 14, and a top layer sheet 16. Recess pockets 18 are formed in the top surface of bottom layer sheet 12 forming chambers 20 for receiving a liquid sample of a particular antigen 22. The thickness of membrane sheet 14 and bottom layer sheet 12 would be approximately 0.001 inches.

Top layer sheet 16 has a plurality of apertures 30 positioned above each of the chambers 20 and these apertures are preferrably spaced one inch from each other. Pushbutton needle assemblies 32 are formed from a disk-shaped pushbutton 34 having a width D1 that is less than the width D2 of apertures 30. Integrally connected flexible support arms 36 have one of their ends connected to the wall of apertures 30 and the other end is connected to the disk-shaped pushbutton 34. A needle 38 extends downwardly from the bottom surface of the disk-shaped pushbutton. The thickness of top layer sheet 16 is T1. At least two of the side edges of the various layers of sheet material are heat sealed or otherwise secured to each other to form an open space 40 between the bottom surface of top layer 16 and the top surface of membrane sheet 14. A protector sheet 50 is removably received in open space 40 to prevent the needle 38 from penetrating membrane sheet 14 prior to its time of intended use.

What is claimed is:

1. A disposable allergy skin testing kit comprising:
   an elongated bottom layer sheet having a top surface, a bottom surface, a front edge, a rear edge, and laterally spaced side edges;

an elongated membrane sheet having a top surface, a bottom surface; a front edge, a rear edge, and laterally spaced side edges;

a plurality of individual sealed chambers formed between the bottom surface of said membrane sheet and the top surface of said bottom layer sheet, a predetermined amount of antigen located in each of said sealed chambers;

the bottom surface of said membrane sheet being in contact with the top surface of said bottom layer sheet;

an elongated top layer sheet having a top surface, a bottom surface, a front edge, a rear edge and laterally spaced side edges, a plurality of apertures formed in said top layer sheet at predetermined positions located respectively above said individual sealed chambers that contain an antigen, a pushbutton needle assembly positioned in each aperture, said pushbutton needle assemblies each having a disk-shaped pushbutton having a bottom surface with a needle extending downwardly therefrom and a plurality of flexible support arms having one of their ends connected to said disk-shaped pushbutton and their other end connected to said top layer sheet adjacent the edges of said apertures; and said top layer sheet, said disk-shaped pushbutton and its needle, and said flexible arms all being integrally formed as a single member of the same material.

2. A disposable allergy skin testing kit as recited in claim 1 further comprising means for connecting at least one of the edges of the top layer sheet and bottom layer sheet together.

3. A disposable allergy skin testing kit as recited in claim 2 wherein there is a predetermined open space formed between the bottom surface of said top layer sheet and the top surface of said membrane sheet.

4. A disposable allergy skin testing kit as recited in claim 3 further comprising an elongated protector sheet that is removably received in the open space formed between the bottom surface of said top layer sheet and the top surface of said membrane sheet.

5. A disposable allergy skin testing kit as recited in claim 1 wherein said bottom layer sheet is made of metallic material.

6. A disposable allergy skin testing kit as recited in claim 5 wherein said membrane is made of metallic material.

7. A disposable allergy skin testing kit as recited in claim 1 wherein said top layer sheet is made of plastic material.

* * * * *